(12) United States Patent
Polloni et al.

(10) Patent No.: US 10,517,328 B2
(45) Date of Patent: Dec. 31, 2019

(54) ELECTRIC CARTRIDGE FOR ELECTRONIC CIGARETTE AND ELECTRONIC CIGARETTE

(71) Applicant: G.D S.p.A., Bologna (IT)

(72) Inventors: Roberto Polloni, Modigliana (IT); Ivan Eusepi, Castelmaggiore (IT); Luca Federici, Bologna (IT)

(73) Assignee: G.D S.P.A., Bologna (IT)

( * ) Notice: Subject to any disclaimer, the term of this patent is extended or adjusted under 35 U.S.C. 154(b) by 61 days.

(21) Appl. No.: 15/565,564

(22) PCT Filed: Apr. 13, 2016

(86) PCT No.: PCT/IB2016/052087
§ 371 (c)(1),
(2) Date: Oct. 10, 2017

(87) PCT Pub. No.: WO2016/166670
PCT Pub. Date: Oct. 20, 2016

(65) Prior Publication Data
US 2018/0116285 A1 May 3, 2018

(30) Foreign Application Priority Data

Apr. 13, 2015 (IT) .............................. BO2015A0174

(51) Int. Cl.
*A24F 13/00* (2006.01)
*A24F 17/00* (2006.01)
(Continued)

(52) U.S. Cl.
CPC ........... *A24F 47/008* (2013.01); *A61M 15/06* (2013.01)

(58) Field of Classification Search
CPC .............................. A24F 47/008; A61M 15/06
(Continued)

(56) References Cited

U.S. PATENT DOCUMENTS 5,322,075 A 6/1994 Deevi et al.
5,408,574 A * 4/1995 Deevi .................. A24F 47/008
128/202.21
(Continued)

FOREIGN PATENT DOCUMENTS

AT 509046 A4 6/2011
CN 102883766 A 1/2013
(Continued)

OTHER PUBLICATIONS

International Search Report dated Jul. 14, 2016 for counterpart PCT Application No. PCT/IB2016/052087.
(Continued)

*Primary Examiner* — Abdullah A Riyami
*Assistant Examiner* — Thang H Nguyen
(74) *Attorney, Agent, or Firm* — Shuttleworth & Ingersol, PLC; Timothy J. Klima (57) ABSTRACT

An electric cartridge for an electronic cigarette including a piece of flexible substrate material including at least a flexible film which mounts an electrically conductive network in the form of an array and defining a plurality of resistive zones (pixels) and a plurality of power supply pins for supplying one or more electric currents and connected to the resistive zones. The resistive zones define heating means and are grouped into distinct modules. Each module corresponds to an uninterrupted portion of the electrically conductive network and includes at least one resistive zone and respective power supply pins. The electric cartridge includes a plurality of portions of aromatic substance positioned on at least one face of the piece of flexible material. Each portion is associated with a resistive zone and positioned in proximity to a heating surface of the respective resistive zone.

20 Claims, 9 Drawing Sheets

(51) Int. Cl.
*A24F 25/00* (2006.01)
*A24F 47/00* (2006.01)
*A61M 15/06* (2006.01)

(58) Field of Classification Search
USPC .................................. 131/328, 329
See application file for complete search history.

(56) References Cited

U.S. PATENT DOCUMENTS

| | | | | |
|---|---|---|---|---|
| 8,881,737 B2 * | 11/2014 | Collett | ................... | H05B 3/265 |
| | | | | 131/328 |
| 9,555,199 B2 | 1/2017 | Buchberger | | |
| 2013/0276804 A1 * | 10/2013 | Hon | ................... | H05B 1/0244 |
| | | | | 131/329 |
| 2014/0060554 A1 * | 3/2014 | Collett | ................... | H05B 3/265 |
| | | | | 131/328 |
| 2014/0202477 A1 * | 7/2014 | Qi | ................... | A24F 47/008 |
| | | | | 131/329 |

FOREIGN PATENT DOCUMENTS

| | | |
|---|---|---|
| CN | 203353674 | 12/2013 |
| EP | 0488488 A1 | 6/1992 |
| WO | WO2013098405 A2 | 7/2013 |
| WO | WO2015000974 A1 | 1/2015 |
| WO | WO2015038981 A2 | 3/2015 |

OTHER PUBLICATIONS

Office Action issued by the Chinese Patent Office dated Aug. 28, 2019 for counterpart Chinese Patent Application No. 201680034288.1.

* cited by examiner

ELECTRIC CARTRIDGE FOR ELECTRONIC CIGARETTE AND ELECTRONIC CIGARETTE

This application is the National Phase of International Application PCT/IB2016/052087 filed Apr. 13, 2016 which designated the U.S.

This application claims priority to Italian Patent Application No. BO2015A000174 filed Apr. 13, 2015, which application is incorporated by reference herein.

TECHNICAL FIELD

This invention relates to an electric cartridge for an electronic cigarette flavoured with aromatic substances.

The invention also relates to an electronic cigarette.

BACKGROUND ART

This invention addresses the sector of what have come to be known as electronic cigarettes. This term is used to denote devices which provide an alternative to traditional smokers' articles and allow users to recreate the gestures and feeling of smoking traditional smokers' articles.

An electronic cigarette can be likened to a vaporizing device which produces an aerosol containing one or more aromatic substances transported by a flow of carrier vapour. In the context of this invention, the term "vaporization" is used to mean, generally speaking, the production of a gas phase. Such production of a gas phase may occur as a result of vaporization in the strict sense (transition of a substance from the liquid to the gas phase) or as a result of sublimation (transition of a substance from the solid to the gas phase).

Usually, the gas phase is produced by heating a starting substance contained in a replaceable cartridge or refill.

Electronic cigarettes can be broadly divided into two different types, according to the form which the vaporizable substance contained in the refill comes in. In a first type of electronic cigarettes, the starting composite substance is in liquid form, whilst in the second type of electronic cigarettes, the starting composite substance is in solid form.

In the first type, the liquid refill is heated by resistance heating. The liquid part vaporizes to form the vapour which carries the aerosol defined on the basis of the aromatic substances contained in the refill. An electronic cigarette of the first type is described in document US20130276804.

The Applicant has noticed that one disadvantage of electronic cigarettes based on liquid refills is the need to manage the preparation and distribution of refills which require containers or tanks. Moreover, although a user has a variety of flavours to choose from, only one refill, and hence one flavour, can be used at a time.

Document WO2013098405 provides an example of a second type of electronic cigarettes, involving the use of a mixture or blend of tobacco which is heated by a metallic plate or element which is in turn heated by an electric circuit. A part of the tobacco mixture has a vaporizable content which produces the carrier vapour which transports the aromatic substances.

Document U.S. Pat. No. 5,322,075 provides another example of the second type of electronic cigarettes where the heating elements are connected to each other by electrical connections. The flavour generating composite, which is based on aromatic substances, is heated and vaporized by the heating elements.

The Applicant has noticed that even electronic cigarettes based on solid refills give the user a limited choice of flavours and come in relatively rigid, standard configurations, in particular with regard to the choice and control of the aromatic substance during use of the cigarette. Document U.S. Pat. No. 5,322,075 in particular involves an electric circuit divided between electrical connectors and heating elements which limits its applicability to simple, predetermined shapes, thus limiting the versatility of use of the cigarette.

DISCLOSURE OF THE INVENTION

In this context, the basic technical purpose of this invention is to provide an electric cartridge for an electronic cigarette and an electronic cigarette, which are versatile and reliable and which allow effective vaporization, meaning by that the production of a gas phase capable of satisfying the increasingly stringent requirements of users.

The purpose specified is substantially achieved by an electric cartridge for an electronic cigarette and an electronic cigarette comprising technical features set out in the present disclosure.

BRIEF DESCRIPTION OF THE DRAWINGS

The invention is described below with reference to the accompanying drawings, which illustrate a non-limiting embodiment of it and in which.

DETAILED DESCRIPTION OF PREFERRED EMBODIMENTS OF THE INVENTION

Figure 1:
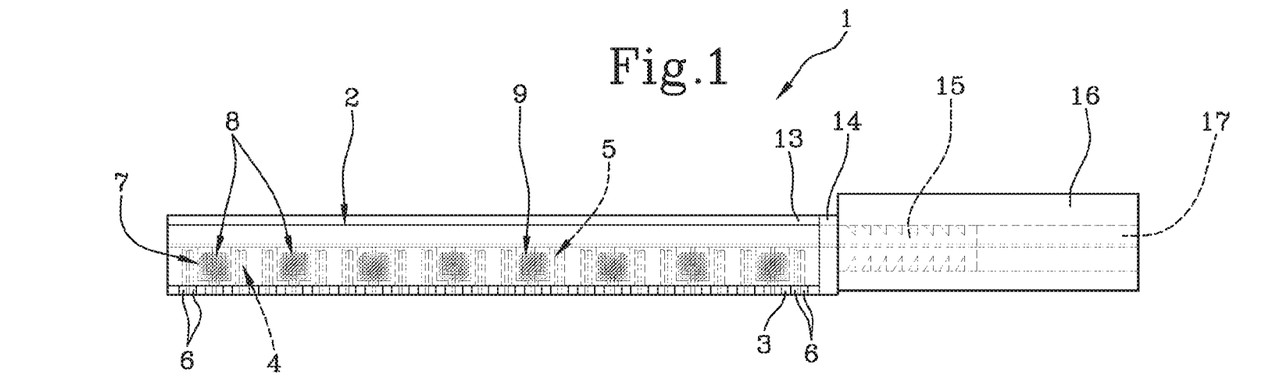
FIG. 1 shows a side view of a first possible embodiment of an electric cartridge according to this invention.
Figure 2:
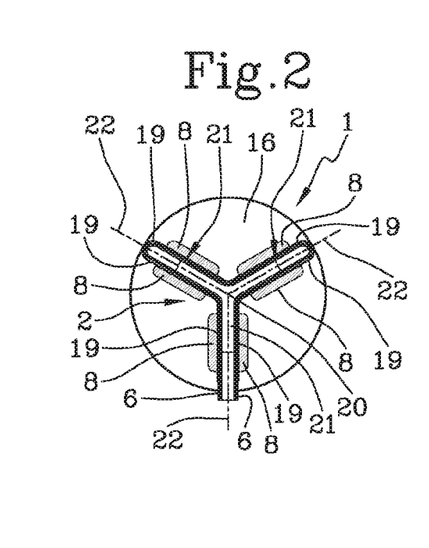
FIG. 2 shows a front view of the electric cartridge of FIG. 1.
Figure 3:
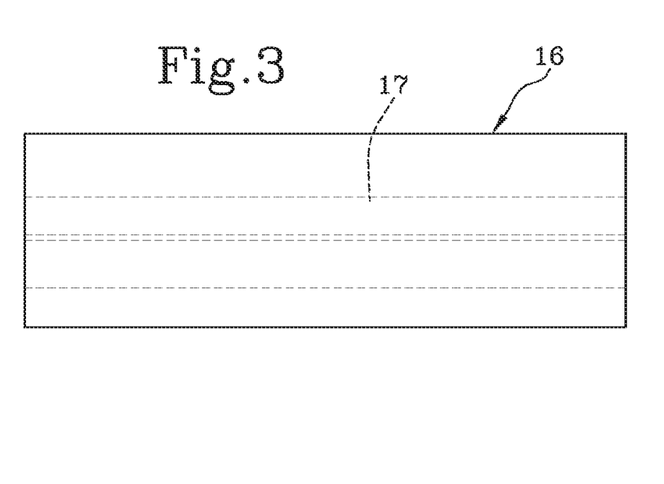
FIG. 3 shows a side view of a component of the electric cartridge of FIG. 1.
Figure 4:
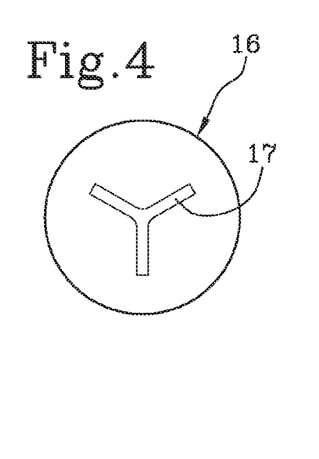
FIG. 4 shows a front view of the component of FIG. 3.
Figure 7:
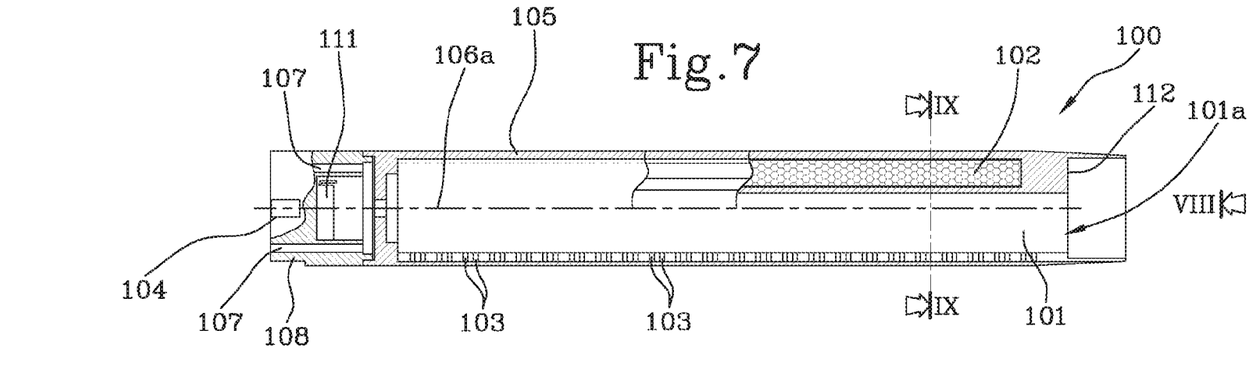
FIG. 7 shows a longitudinal cross section of a possible embodiment of an electronic cigarette according to this invention.
Figure 8:
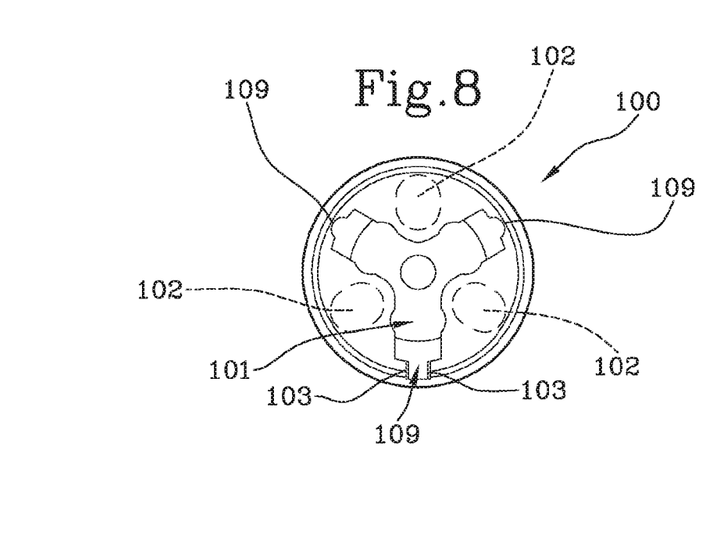
FIG. 8 shows a front view of the electronic cigarette of FIG. 7 from the side indicated by the arrow VIII.
Figure 9:
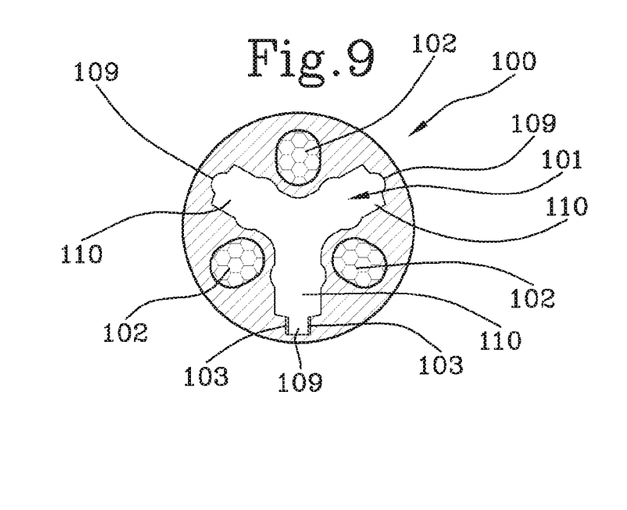
FIG. 9 shows a transverse cross section of the electronic cigarette of FIG. 7 through the line IX-IX.

The numeral 1 in FIGS. 1 and 2 denotes in its entirety an electric cartridge for holding aromatic substances and suitable for use in an electronic cigarette 100, illustrated for example in FIGS. 7-9.

The term "electronic cigarette" is used to mean an electronic device for smokers, commonly known as "e-cigarette", of any shape and size, and whose use and function can be substantially likened to those of a traditional cigarette made from tobacco. Preferably, this device has cylindrical shape and size comparable to those of a traditional cigarette, is used as a surrogate or alternative to cigarettes and is designed to release a flavoured vapour or aerosol.

Figure 5:
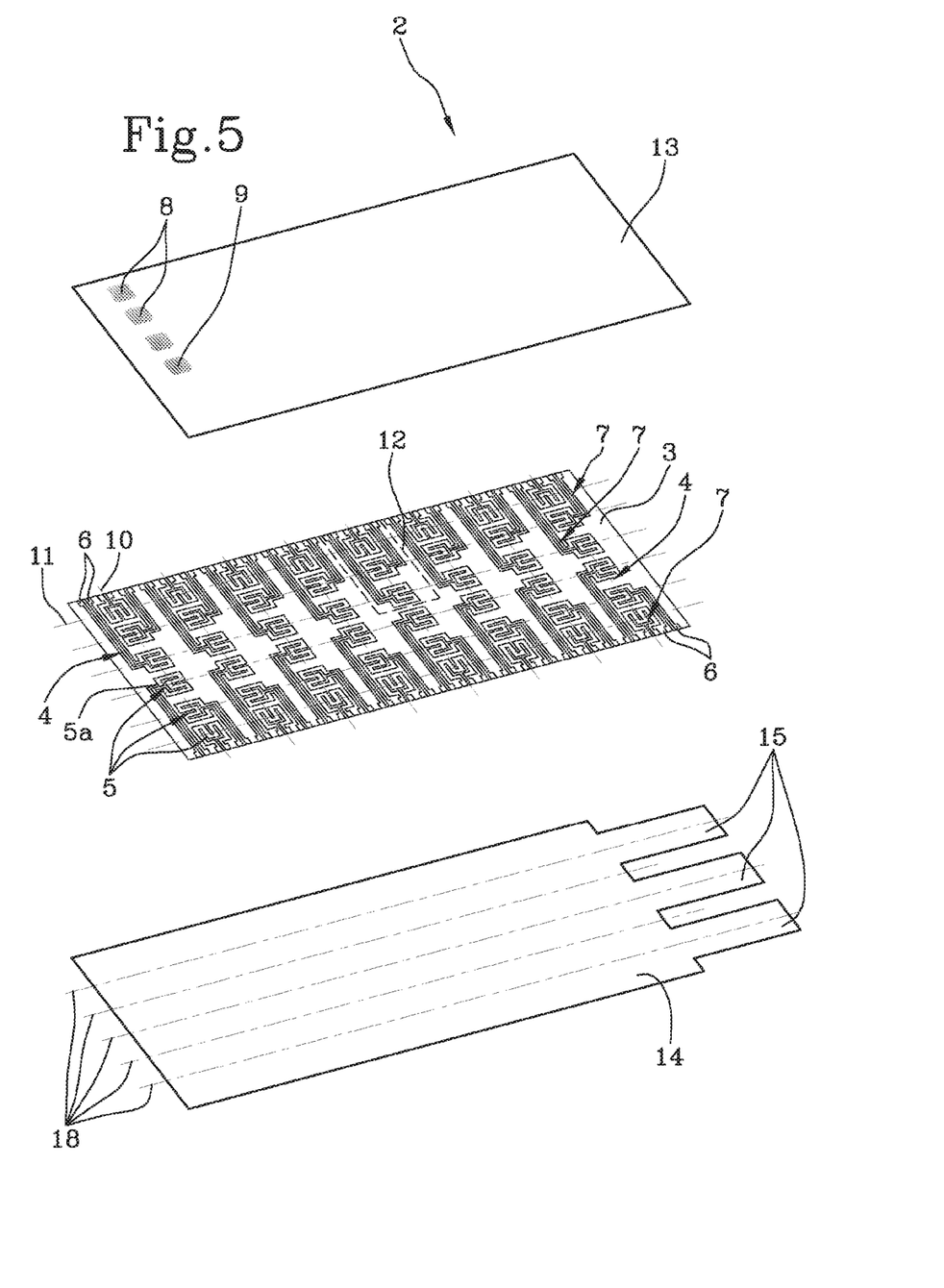
FIG. 5 shows an exploded perspective view of a component of the electric cartridge of FIG. 1.
Figure 6:
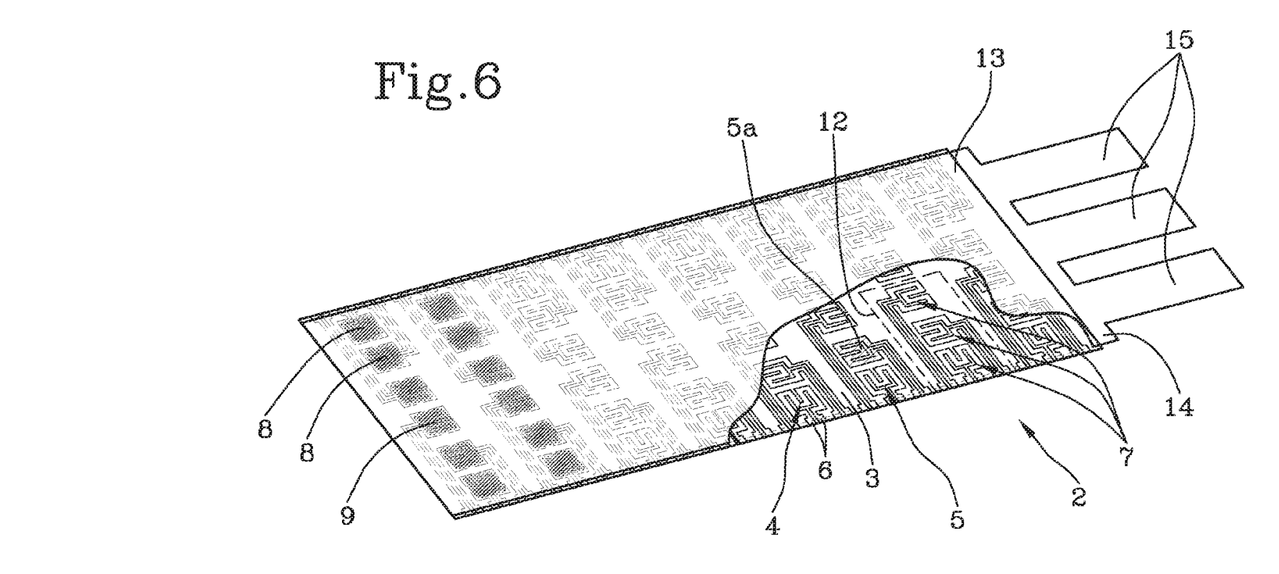
FIG. 6 shows a perspective view of the component of FIG. 5 when assembled.

The electric cartridge 1 comprises a piece 2 of flexible substrate material illustrated in detail in FIGS. 5 and 6. The piece 2 comprises a flexible film 3 which mounts an electrically conductive network 4. The flexible film 3 is, for example, a film of plastic material resistant to high temperatures of between approximately 250° C. and 300° C. More specifically, the flexible film may be made of a polyimide material. The thickness of the flexible film 3 is preferably approximately 0.1 mm.

The electrically conductive network 4 is in the form of an array and defines a plurality of resistive zones 5 and a plurality of power supply pins 6 for supplying one or more electric currents and connected to the resistive zones 5. For clarity, only some of the resistive zones and power supply pins are numbered in the accompanying drawings.

In the example embodiment shown in the accompanying drawings, the power supply pins 6 are located on opposite sides of the piece 2. Alternatively, they might be located on adjacent sides or only on one side of the piece 2.

The electrically conductive network 4 may be printed on the flexible film 3 or applied thereto by other techniques.

The resistive zones 5 define heating means, in particular a heating surface 5a. Further, the resistive zones 5 are grouped into distinct modules 7. In the example embodiment illustrated, each module 7 comprises a resistive zone 5 and two power supply pins 6.

Each module 7 corresponds to an uninterrupted portion of the electrically conductive network, that is to say, is made by continuous printing or deposition of a single conductive material. Each resistive zone 5 is preferably made by depositing the conductive material along a winding path defining the heating surface 5a or increasing the surface extension of the conductive material, uninterruptedly along the path.

The piece 2 of flexible material which is used as substrate may comprise insulating points obtained by deposition/printing on possible crossing points of the electrically conductive network 4. Alternatively, the flexible film 3 may be a multilayer flexible printed circuit, with the electrically conductive network 4 made on two or more separate layers with interposed insulating layers.

The numeral 8 denotes portions of aromatic substance positioned on one face of the piece 2 of flexible material. Each portion 8 of aromatic substance is associated with one resistive zone 5 and positioned at the heating surface 5a of the respective resistive zone.

It is possible to use a composite containing the same aromatic substance, for example made by premixing flavours/substances constituting the recipe, for all the portions 8, hence for all the modules 7. Alternatively, the aromatic substance, for example a single flavour, of a first module might be different from the aromatic substance, for example a single flavour, of a second, distinct module. Further, a plurality of different aromatic substances might be distributed among the different modules.

It should be noted that the electrically conductive network 4 may be made in the form of a passive array comprising a plurality of arrays, each dedicated to a particular aromatic substance (for example, an array of nicotine points, one of menthol points, and so on).

Alternatively, the electrically conductive network 4 may be made in the form of an active array where each portion 8 of aromatic substance is associated with a dedicated, bistable memory circuit which keeps its "ON" state until next command. In this case, the controlling array, which is one for all, is scanned very rapidly to cause vaporizing (or rather sublimating) of the desired portions 8 one at a time. The controlling array is then scanned a second time for switching off.

Preferably, the portions 8 of aromatic substance are obtained by deposition of a composite containing an aromatic substance (for example, by jet printing a composite containing an aromatic substance, deposition of a fluid filament, rotogravure printing). Depending on the composite used, the portions 8 may be entirely solid or partly solid with a solid outer layer enclosing a liquid or semiliquid centre. In the first case, vaporization (that is, the production of a gas phase) is the result of sublimation of the solid composite. In the second case, vaporization (that is, the production of the gas phase) is the result partly of the sublimation of the outer layer and partly of the vaporization proper of the liquid or semiliquid centre.

For example, the aforementioned printing may be obtained by a printing process which is similar, or can be likened, to inkjet printing, where droplets of the composite are propelled onto the printing substrate. Each portion 8 may be made up of one or more superposed or juxtaposed layers, each made in one depositing pass, for example a jet printing pass, and comprising an aromatic substance selected on the basis of a predetermined recipe. In a possible embodiment, there may be one or more portions 9 of a volatilizable substance suitable for releasing basic or carrier vapour, leaving to the portions 8 only the function of supplying the aromatic substance.

As illustrated in FIGS. 5 and 6, for example, the resistive zones 5 are arranged along a plurality of rows 10 and columns 11 obtained by sequential and/or mirror-symmetric repetition of a group 12 of modules 7 of resistive zones. In the example illustrated, the group 12 is repeated both sequentially along the direction of the columns 11 and mirror-symmetrically to form a row 10. The rows and columns may be made on two or more separate layers with insulating layers interposed between them in a flexible film 3 made in the form of a multilayer printed circuit.

The piece 2 of flexible substrate material may be perforated with a mesh of a size suitable for allowing air to pass through it correctly.

As illustrated in FIGS. 5 and 6, for example, the piece 2 of flexible substrate material may comprise a covering film 13 located on the electrically conductive network 4 to isolate it from the portions 8 of aromatic substance positioned on the covering film itself. The dimensions of the covering film 13 are such as to leave the power supply pins 6 uncovered. The covering film 13 is made of a material suitable for electrically insulating the electrically conductive network 4 and preferably preventing the electrically conductive network 4 from releasing harmful substances.

In an alternative not illustrated, the electrically conductive network 4 is positioned on one face of the flexible film 3 and the portions 8 of aromatic substance are positioned on the opposite face of the flexible film so that the flexible film 3 is interposed between the electrically conductive network 4 and the portions 8 of aromatic substance, performing the function of the flexible film 13.

As illustrated in FIGS. 5 and 6, for example, the piece 2 of flexible substrate material may comprise a base sheet (14) coupled to the flexible film 3 on the side opposite to the portions 8 of aromatic substance. The dimensions of the base sheet 14 are such as to leave the power supply pins 6 uncovered. The base sheet 14 may be made of paperboard and may be coupled to the flexible film 3 for example by a layer of adhesive material, not illustrated, chosen according to its heat stability, which must be greater than that needed to vaporize the portions 8. In the example of FIGS. 5 and 6, the base sheet 14 comprises fastening extensions 15 to which a filter 16 of the electric cartridge 1 is permanently fixed. Permanent fixing may be accomplished by a shape fit comprising a socket 17 in the filter 16 suitably shaped to receive the fastening extensions 15 and further secured for example by gluing or the provision of a suitably sawtoothed profile of the fastening extensions 15.

In the electric cartridge 1, the piece 2 may be kept stretched or shaped in such a way as to contain the transverse dimensions of the electric cartridge itself.

In the example illustrated in FIGS. 1 and 2, the piece 2 of flexible substrate material is folded in concertina fashion along fold lines 18 illustrated by way of example in FIG. 5 with reference to the base sheet 14. The fold lines 18 delimit respective panels 19 of the concertina. Each column 11 of resistive zones 5 occupies one panel 19 of the concertina. Further, the piece 2 of flexible substrate material is wound about a longitudinal axis 20 parallel to the fold lines 18. In winding the piece 2, the panels 19 of the concertina are grouped in pairs 21 of parallel, juxtaposed panels at the face opposite to the portions 8 of aromatic substance. The pairs 21 of panels are arranged along directions 22 radial to the longitudinal axis 20. In the example illustrated, there are three pairs 21 of panels arranged at 120° from each other. In other words, the piece 2 is folded and wound to form a transverse cross section with arms arranged radially, for example in the shape of a Y, of the same length and equally spaced from each other.

In an alternative embodiment, not illustrated, the piece 2 is folded in concertina fashion and is kept in a flat shape, that is to say, not wound about the longitudinal axis.

Figures 16, 17:
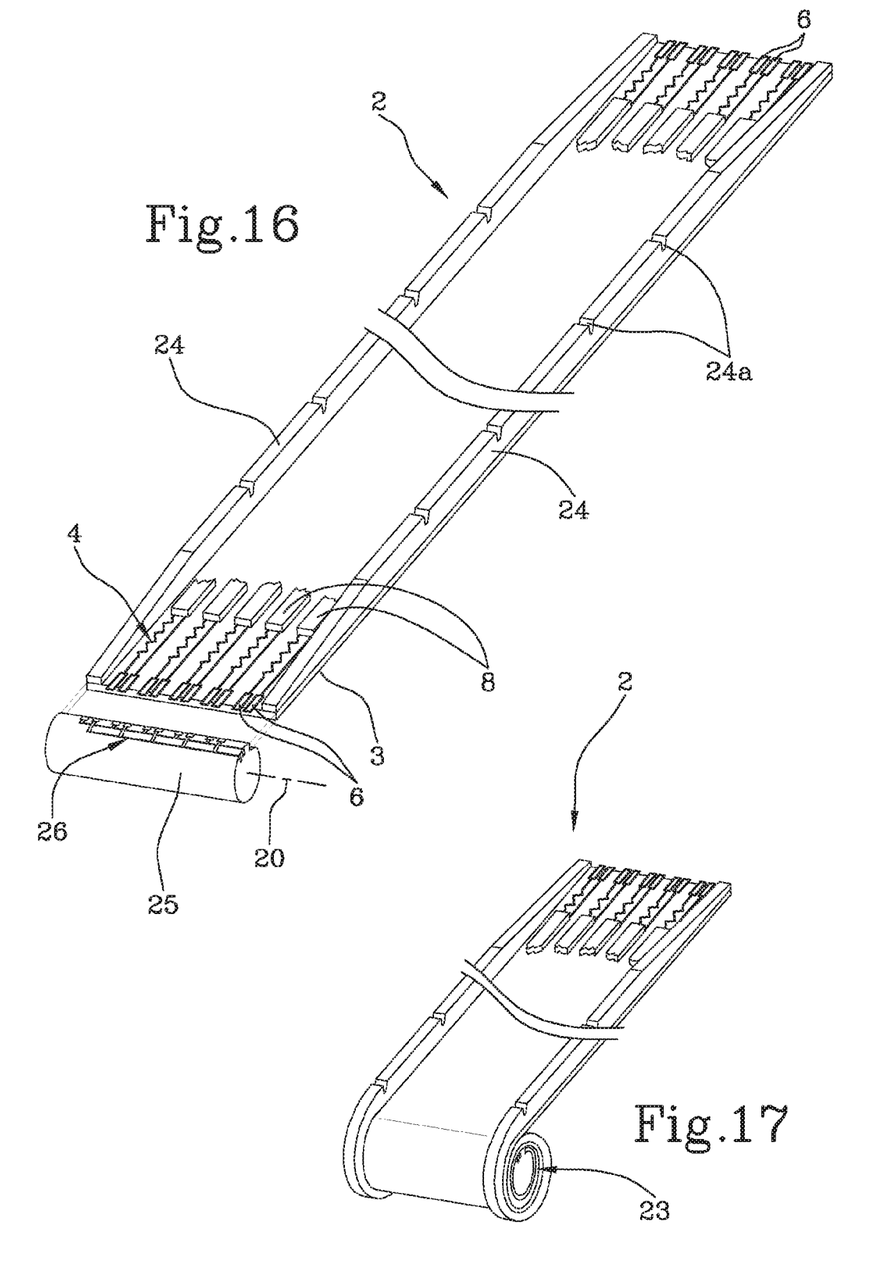
FIGS. 16 and 17 are schematic views showing a further possible embodiment of an electric cartridge according to this invention.

FIGS. 16-17 illustrate a variant embodiment in which the piece 2 is not folded in concertina fashion but is wound about a longitudinal axis 20, leaving the portions 8 of aromatic substance preferably directed outwards relative to the longitudinal axis 20. In this case, the winding comprises a plurality of superposed coils 23 preferably spaced from each other by supporting shoulders 24 located on opposite, end sides of the piece 2. The supporting shoulders 24 comprise notches 24a adapted to facilitate winding in coils and to create passages for the air which strikes the portions 8.

Alternatively, the piece 2 of flexible substrate material is wound into the shape of a cylindrical surface.

The power supply pins may be made both on the ends of the piece 2 and on directrices of the cylindrical or coiled surface.

In the cases where the piece is wound, in particular in the case shown in FIGS. 16 and 17, the piece may be wound around an inner core 25. The inner core 25 preferably comprises a plurality of electrical contacts 26 adapted to power the power supply pins 6 and/or a local processing unit—for example a chip—configured to control the power supply of the modules 7 of the electrically conductive network 4 as a function of a particular power supply program, as described below with reference to the modes of using the electric cartridge and the electronic cigarette.

In one possible embodiment, the electric cartridge 1 may comprise means for recognizing the state of the electric cartridge and/or of the portions 8 and configured to record/ provide information regarding the state (new/used) of the electric cartridge itself. In a first embodiment, the recognition means comprise a static, non-volatile memory which is structurally integrated in the electric cartridge 1 and configured to maintain its state even in the absence of power supply.

In an alternative solution, the recognition means comprise a storage element—for example a fuse—associated with the electrically conductive network 4 and with each resistive zone 5.

Figure 15:
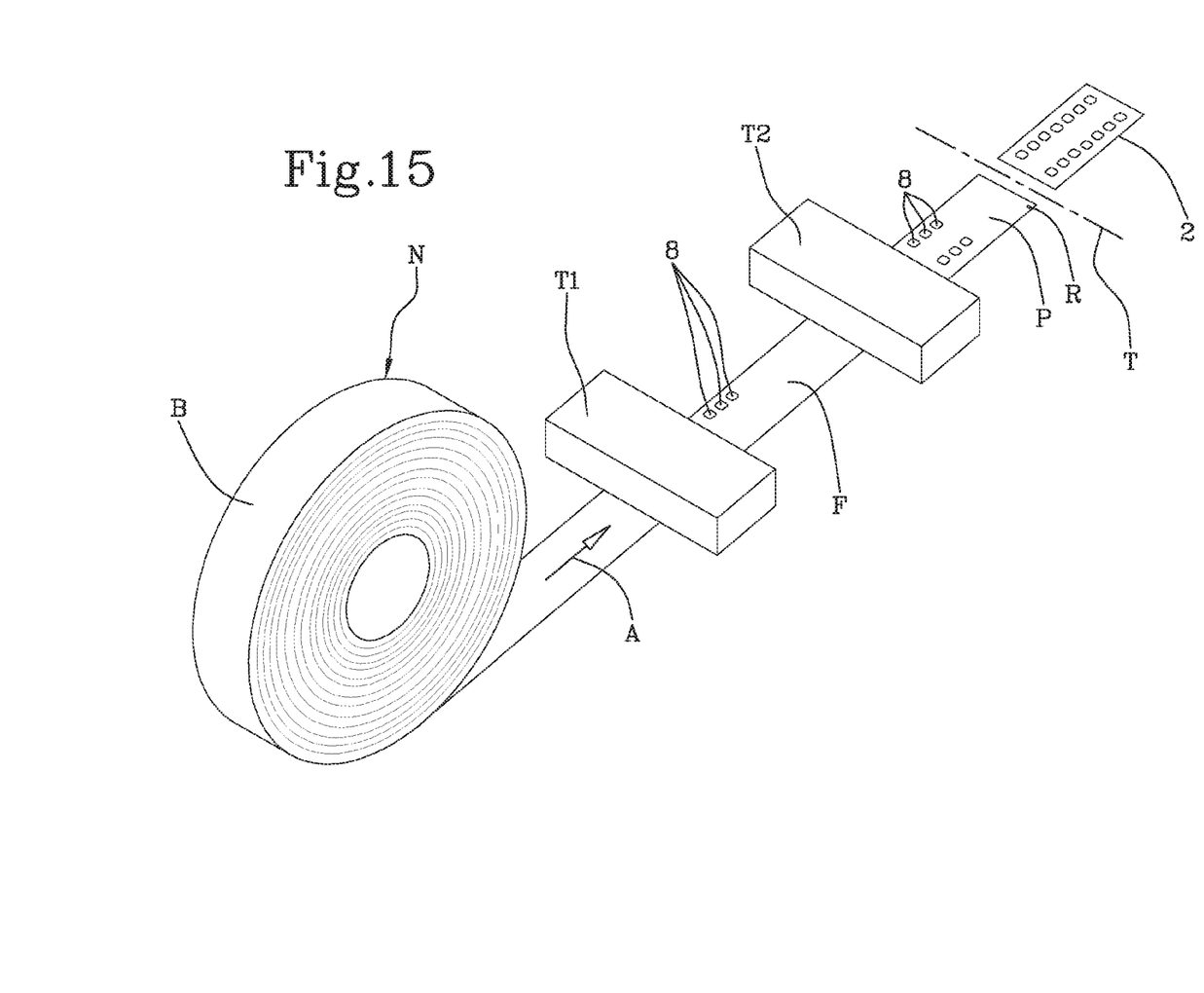
FIG. 15 schematically represents a step of the making method according to this invention.

The electric cartridge 1 can be made from a continuous web N of flexible substrate material comprising at least one layer of flexible film 3 mounting a plurality of modules 7 of electrically conductive networks 4. The continuous web N is, for example, wound on a roll B, as illustrated in FIG. 15.

The continuous web N may be prepared in advance by coupling a continuous web of flexible film 3 to a continuous web of covering film 13 placed on the electrically conductive networks 4. Alternatively, there is a step of coupling the continuous web of flexible film 3 to the continuous web of covering film 13, not illustrated in FIG. 15.

The continuous web N may also be prepared in advance by coupling the continuous web of flexible film 3 to a continuous web of base sheet 14 placed on the face opposite to that where the portions 8 will be placed. Alternatively, there is a step of coupling the continuous web of flexible film 3 to the continuous web of base sheet 14, not illustrated in FIG. 15.

The continuous web N of flexible substrate material is made to advance along a feed path A along which it meets one or more deposition heads for depositing a composite containing an aromatic substance.

For example, the deposition heads may be like those used for jet printing designed to propel droplets of composite on the printing substrate to deposit on the continuous web doses of a composite comprising an aromatic substance, in proximity to the heating surface 5a of the resistive zones 5 in order to obtain portions 8 of aromatic substance. FIG. 15 shows two deposition heads T1, T2 for depositing doses of a composite containing different aromatic substances to form different portions 8 at different modules 7. More specifically, at least one dose of a composite comprising an aromatic substance is deposited on the continuous web in proximity to the heating surface 5a of a resistive zone 5, and at least one dose of a composite comprising a different aromatic substance is deposited on the continuous web in proximity to the heating surface 5a of a resistive zone 5 of a second distinct module.

Deposition is accomplished in phase with the array of resistive zones 5, for example by providing a centring notch R or an optically recognizable element, or by including a step of acquiring the pattern of the resistive zones by means of a vision system which allows controlling deposition in a "synchronous" manner.

Alternatively, the deposition heads may be used to deposit different layers, juxtaposed or superposed, of the same portion 8.

One of the deposition heads may be used to deposit on the continuous web at least one dose of a composite comprising a volatilizable substance suitable for releasing basic or carrier vapour in order to obtain at least one portion 9 of volatilizable substance.

In the example illustrated in FIG. 15, the face F of the continuous web N which the portions 8 are deposited on may be a face of the layer of flexible film 3 opposite to the electrically conductive networks 4 or a face of the covering film 13. Alternatively, the portions 8 are deposited directly on the heating surfaces 5a of the resistive zones 5.

Cutting means are provided along the feed path A for cutting an end portion P of the continuous web N along a cutting line T to obtain a piece 2 of flexible substrate material containing a predetermined number of modules 7. As reference for the cutting step it is possible to use the same centring notch as that used for synchronizing the deposition step.

The piece 2 may be shaped to adapt to the required shape of the electric cartridge 1. In particular, it may be wound in coils and/or folded in concertina fashion.

Alternatively, pre-cut pieces 2 may be made to advance along the feed path A for the portions 8 and/or the portions 9 to be deposited on them.

The portions 8 and/or the portions 9 may be made using different deposition techniques other than jet printing.

Alternatively, making the electric cartridge 1 may involve continuously making the electrically conductive network 4 on the continuous web of flexible film 3.

With reference to FIGS. 7-9, one possible embodiment of the electronic cigarette 100 comprises a housing 101 open to the outside at an inlet 101a and adapted to receive the electric cartridge 1.

The electronic cigarette 100 comprises electrical power supply means, in particular one or more batteries 102. In the example illustrated, there are three batteries 102.

The electrical power supply means are connected to a plurality of electrical contacts 103 which lead into the housing 101 in such a way as to power the power supply pins 6 of the electric cartridge 1 when it is inserted into the electronic cigarette 100.

External contacts 104 may be provided to recharge the batteries 102. The housing 101 is made inside a body 105, for example made of plastic material, which extends along a main direction of extension 106a coinciding with a main direction of extension of the housing 101 and with a direction of inserting the electric cartridge 1 into the electronic cigarette 100.

The housing 101, in a use configuration of the electronic cigarette, is configured to define grooves 106 (FIG. 12) for the passage and distribution of air and adapted to face the portions 8 of aromatic substance. The grooves 106 are in communication with air inlets 107 leading, for example, in proximity to a far end 108 of the electronic cigarette.

Figure 12:
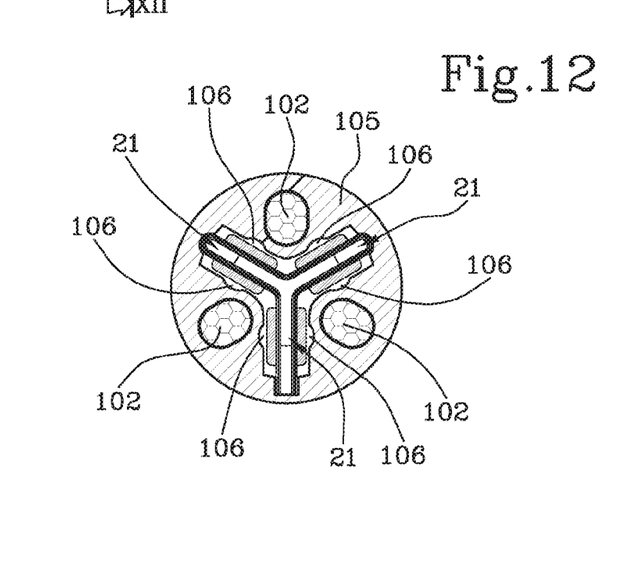
FIG. 12 shows a transverse cross section of the assembly of FIG. 10 through the line XII-XII.

The housing 101 has a transverse cross section (FIGS. 8 and 9) configured to define the grooves 106 which, in a use configuration of the electronic cigarette, are delimited by the walls of the housing 101 and by the electric cartridge 1 (FIG. 12).

The housing 101 comprises, for example, fastening seats 109 adapted to hold the electric cartridge 1 in place in a configuration of use of the electronic cigarette 100. More specifically, the electrical contacts 103 lead into the housing 101 in proximity to one of the fastening seats 109.

If the electric cartridge 1 has a transverse cross section with radial arms, in particular like the one illustrated in FIGS. 1 and 2, the housing 101 comprises a plurality of radial portions 110, each adapted to receive a pair 21 of panels 19 of the electric cartridge 1. Preferably, there is a battery 102 positioned between two radial portions 110 and extending along the main direction of extension of the electronic cigarette 100.

Figure 10:
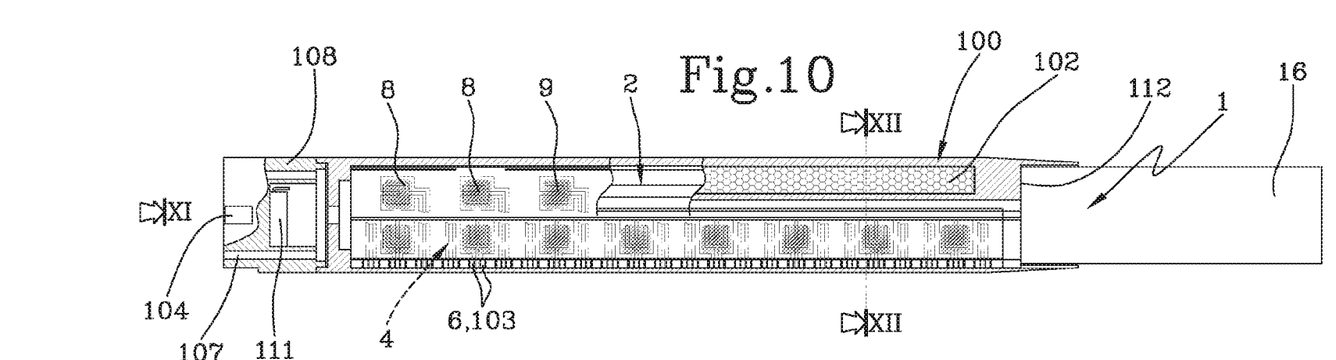
FIG. 10 shows a longitudinal cross section of an assembly comprising the electronic cigarette of FIG. 7 in a configuration of use associated with the electric cartridge of FIG. 1.
Figure 11:
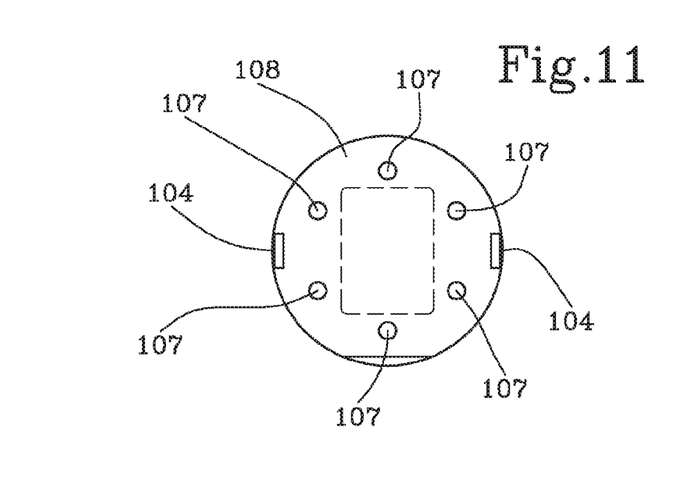
FIG. 11 shows a front view of the assembly of FIG. 10 from the side indicated by the arrow XI.

FIGS. 10-12 show the electronic cigarette 100 in a configuration of use, where the electric cartridge 1 has been inserted into the housing 101. A shoulder 112 in abutment against the filter 16 defines the correct position of the electric cartridge 1 in the electronic cigarette 100.

A local processing unit 111 may be integrated in the electronic cigarette 100 or in the electric cartridge 1, for example in proximity to the core 25, as described above.

The local processing unit 111 is configured to control the electrical power supply of the modules 7 of the electrically conductive network 4 as a function of a particular power supply program, as described below with reference to the modes of using the electric cartridge and the electronic cigarette.

Preferably, the local processing unit 111 comprises a communication module 113 configured to be placed in wireless or wired connection with a communication module of a remote processing unit which are described below with reference to a control system 200 for an electronic cigarette 100 illustrated for example in FIG. 13.

The electronic cigarette 100 may also comprise at least one temperature sensor and/or at least one negative pressure sensor. In this case, the local processing unit 111 comprises a processing module 114 configured to receive data from the temperature sensor and/or from the negative pressure sensor and to control the electrical power supply of the modules 7 of the electrically conductive network 4 as a function of this data.

The purpose of subdivision into distinct functional modules is solely to describe the functionalities of the processing unit clearly and fully. Each processing unit may consist of a single electronic device, suitably programmed to perform the functionalities described, and the different modules may correspond to hardware entities and/or software routines forming part of the programmed device. Alternatively, or in addition, these functionalities may be performed by a plurality of electronic devices over which the aforementioned electronic devices may be distributed. Further, the processing units may use one or more processors to perform the instructions contained in the modules.

The electronic cigarette 100 may also comprise a display or a status LED to indicate the power supply program currently active on the electronic cigarette itself and, as described below, corresponding to a particular "smoking program". The electronic cigarette 100 may also comprise selecting means for selecting the power supply program (and hence the "smoking program") at local level, that is to say, preset on the local processing unit 111.

Using the electric cartridge 1 and the electronic cigarette 100 involves loading the electronic cigarette 100 with an electric cartridge 1 provided with portions 8 in a particular sequence and arrangement. The local processing unit 111 may operate as a function of one or more power supply programs which are predefined and preset or downloaded from a remote processing unit. The preset programs may be selected at local level using the aforementioned selecting means (for example, 3-4 intensity levels and 2-3 usual programs can be selected).

Based on the selection made, the power supply means sequentially feed certain power supply pins 6 or groups of power supply pins 6 to vaporize certain aromatic substances simultaneously and/or sequentially and the display or the status LED indicates the power supply program currently active on the electronic cigarette. More specifically, the modules 7 are selectively powered to follow a predetermined sequence or combination of aromatic substances each time the user inhales.

The selecting means may also be configured to locally modify the "smoking program" even at run time, for example to differentiate the puffs.

For example, by setting the electric cartridge 1 according to predetermined flavour patterns (vanilla, coffee, chocolate, menthol, etc.), it is possible to define a "smoking program" which allows vaporizing only the vanilla flavour, or only the menthol flavour, or a combination corresponding to the current effect of the curing on the tobacco. The power supply program may be activated by the user's inhaling, for example by means of the negative pressure sensor, and may follow predetermined vaporizing sequences, even of different aromatic substances.

Figure 13:
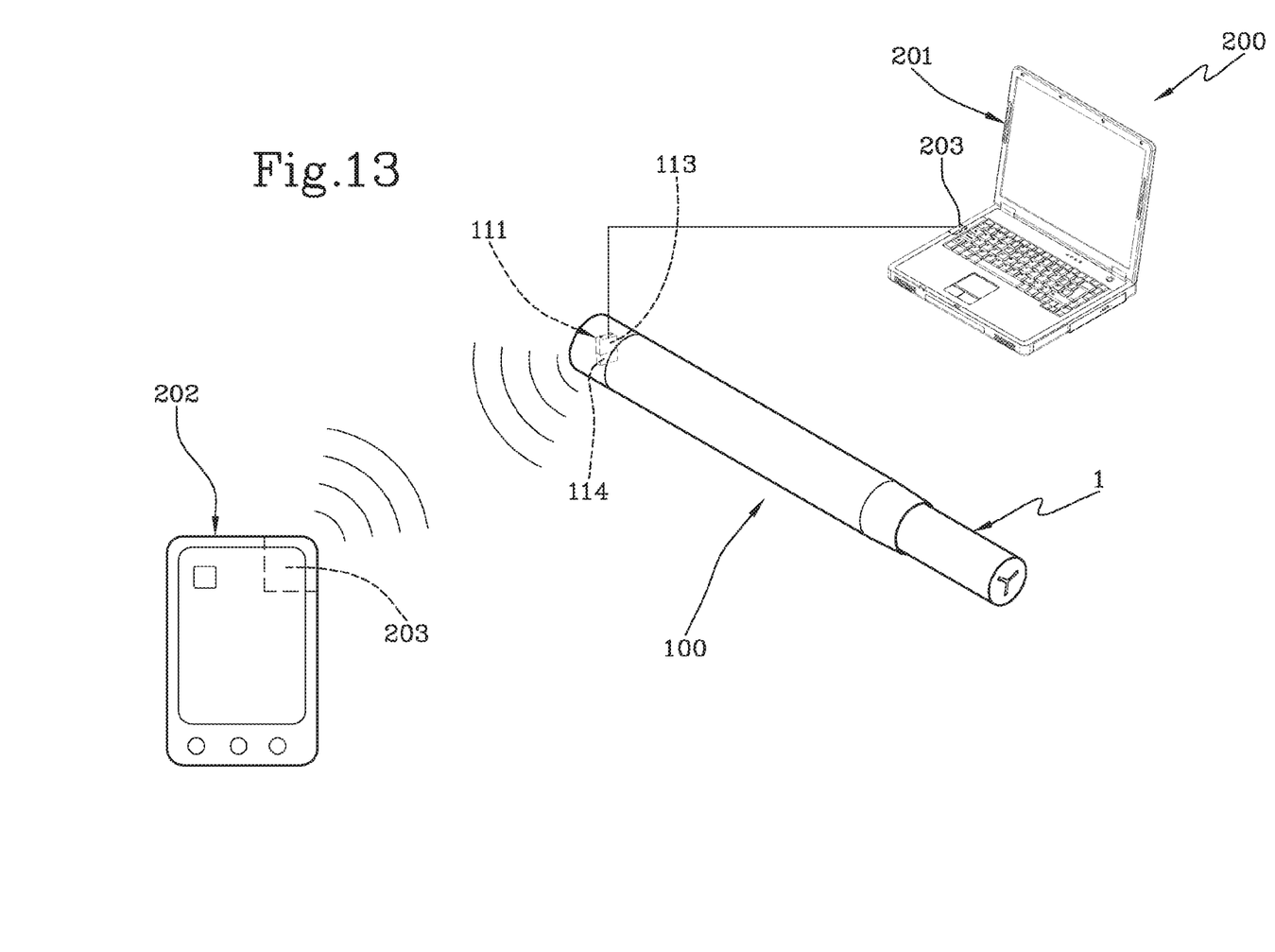
FIG. 13 shows a schematic view of a system for controlling an electronic cigarette.
Figure 14:
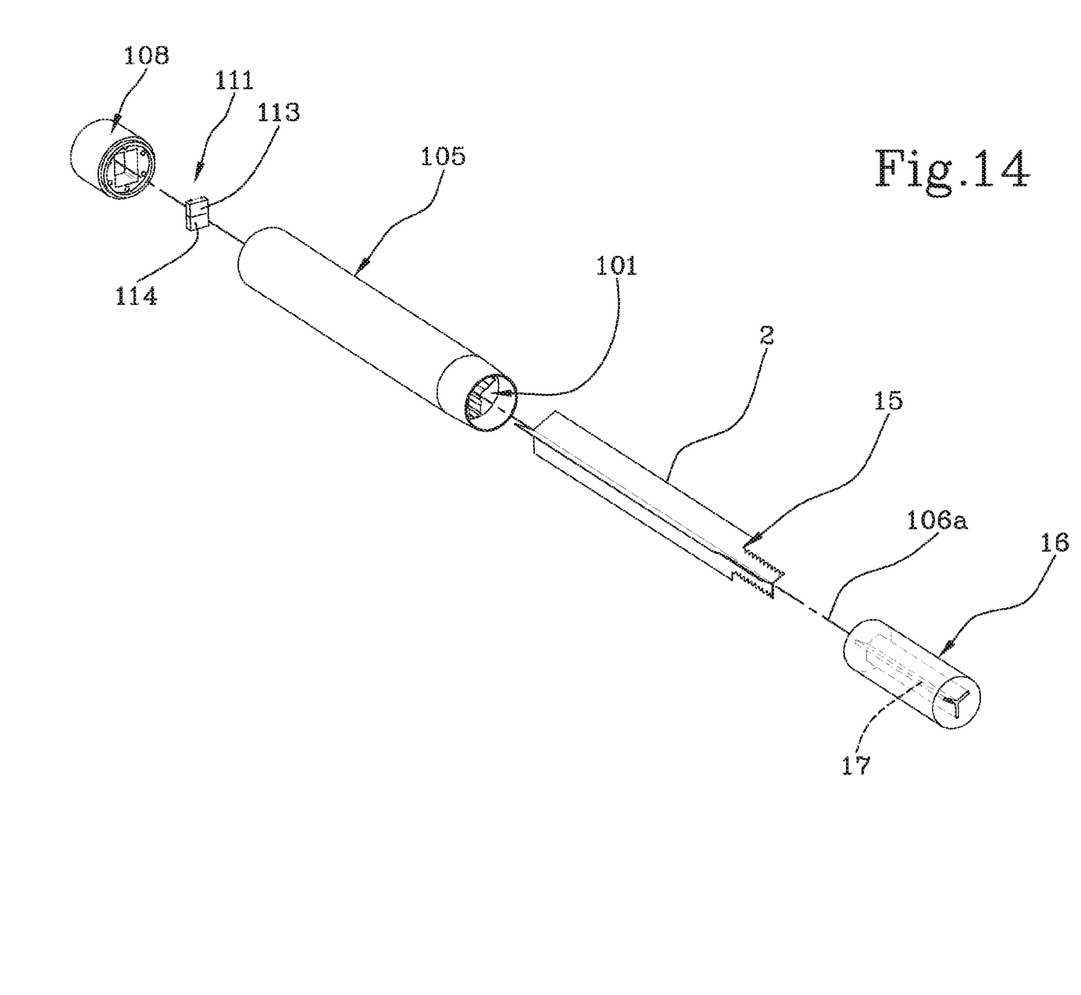
FIG. 14 shows an exploded perspective view of the electronic cigarette.

With reference to FIG. 13, the control system 200 for the electronic cigarette 100 comprises an electronic cigarette 100 provided with a local processing unit 111 comprising a communication module 113. The control system 200 also comprises a remote processing unit, for example defined by a computer 201 or a smartphone 202 and comprising a communication module 203. The remote processing unit is configured to:

a) read the predefined power supply program/programs of the local processing unit 111 by means of a wireless or wired connection between the communication module 203 of the remote processing unit and the communication module 113 of the local processing unit 111;

b) be interfaced with a user to modify the predefined power supply program/programs;

c) modify the predefined power supply program/programs in accordance with user settings thereby determining a modified power supply program/modified power supply programs;

d) transmit the modified power supply program/programs to the local processing unit 111 by means of a wireless or wired connection between the communication module 203 of the remote processing unit and the communication module 113 of the local processing unit 111.

The user can therefore use a software residing in the computer 201 to choose the power supply program suitable for the desired "smoking program", also according to the type of electric cartridge 1. The computer 201 allows carrying out steps b) and c) so that the modified power supply program sent to the local processing unit 111 can run the desired "smoking program".

Similarly, the user can carry out steps b) and c) using an application (app) for a smartphone 202.

More specifically, communication between the electronic cigarette 100 and the remote processing unit can occur by way of near field communication (NFC) technology which allows two-way. short-range wireless connectivity such that communication occurs by moving the electronic cigarette 100 close to, that is "approaching" it, for example to a smartphone. This technology makes it possible to view on the display and/or on the smartphone further information about the active smoking program.

As soon as the power supply program ("smoking program") is downloaded from the remote processing unit, the display or the status LED indicates the currently active smoking program.

It should be noted that the local processing unit 111 can also be configured to scan the portions 8 and to reconstruct the map of those still available (when recognition means are provided) and, for example, tell the user how many puffs and which portions 8 remain.

The invention claimed is:

1. An electric cartridge for an electronic cigarette, comprising:

a piece of flexible substrate material comprising a flexible film which mounts an electrically conductive network in formed as an array and defining a plurality of resistive zones and a plurality of power supply pins for supplying one or more electric currents and connected to the plurality of resistive zones, wherein the electrically conductive network is positioned on a first face of the flexible film;

the plurality of resistive zones defining a heating device and being grouped into distinct modules, each of the distinct modules corresponding to an uninterrupted portion of the electrically conductive network and comprising a resistive zone of the plurality of resistive zones and respective ones of the plurality of power supply pins;

a plurality of portions of aromatic substance positioned on a second face of the flexible film, the second face being opposite the first face on the flexible film, each of the plurality of portions being associated with the resistive zone and positioned in proximity to a heating surface of the resistive zone;

wherein the flexible film is interposed between the electrically conductive network and the plurality of portions of aromatic substance, and wherein the piece of flexible substrate material comprises a base sheet coupled to the flexible film on a side opposite to the plurality of portions of aromatic substance.

2. The electric cartridge according to claim 1, wherein a first module of the distinct modules includes a first portion of aromatic substance of the plurality of portions of aromatic substance that is different from the a second portion of aromatic substance of the plurality of portions of aromatic substance that is included in a second, distinct module of the distinct modules.

3. The electric cartridge according to claim 1, wherein the plurality of portions of aromatic substance are obtained by a deposition head which sprays a composite containing the aromatic substance.

4. The electric cartridge according to claim 3, wherein a portion of the plurality of portions of aromatic substance comprises two or more superposed or juxtaposed layers, each layer comprising a predetermined aromatic substance and made by one depositing pass.

5. The electric cartridge according to claim 1, and further comprising one or more portions of a volatilizable substance suitable for releasing basic or carrier vapor.

6. The electric cartridge according to claim 1, wherein the plurality of resistive zones are arranged along a plurality of rows and columns obtained by at least one chosen from sequential and mirror-symmetric repetition of a group of modules of the plurality of resistive zones.

7. The electric cartridge according to claim 1, wherein the piece of flexible substrate material is wound about a longitudinal axis and wherein the plurality of portions of aromatic substance are directed outwards relative to the longitudinal axis.

8. The electric cartridge according to claim 7, wherein the wound piece of flexible substrate material forms a cylindrical surface or a plurality of superposed coils spaced from each other by supporting shoulders located on opposite, end sides of the piece of flexible substrate material.

9. The electric cartridge according to claim 1, wherein the piece of flexible substrate material is folded in a concertina manner along fold lines delimiting respective panels of the concertina, the plurality of resistive zones being arranged along a plurality of columns, each column occupying a panel of the concertina.

10. The electric cartridge according to claim 9, wherein the piece of flexible substrate material is wound about a longitudinal axis parallel to the fold lines, the panels of the concertina being grouped into pairs of parallel, juxtaposed panels at the face opposite to the plurality of portions of aromatic substance, the pairs of panels being arranged along directions radial to the longitudinal axis, at 120° from each other.

11. The electric cartridge according to claim 1, and further comprising an inner core around which the piece of flexible substrate material is wound, the inner core comprising a plurality of electrical contacts adapted to feed at least one chosen from the power supply pins and a local processing unit configured to control a power supply of the distinct modules of the electrically conductive network as a function of a predetermined power supply program.

12. The electric cartridge according to claim 1, wherein the base sheet comprises a fastening extension to which a filter of the electric cartridge is permanently fixed.

13. An electronic cigarette comprising:
a housing adapted to receive an electric cartridge according to claim 1,
an electrical power supply connected to a plurality of electric contacts adapted to power the power supply pins of the electric cartridge,
a local processing unit integrated in the electronic cigarette and configured to control the electric power supply of the modules of the electrically conductive network as a function of a predetermined power supply program.

14. The electronic cigarette according to claim 13, wherein the local processing unit comprises a communication module configured to be placed in wireless or wired connection with a communication module of a remote processing unit.

15. The electronic cigarette according to claim 13, and further comprising at least one chosen from a temperature sensor and a negative pressure sensor and wherein the local processing unit comprises a processing module configured to receive data from the at least one chosen from the temperature sensor and the negative pressure sensor and to control the electric power supply of the modules of the electrically conductive network as a function of the data.

16. The electronic cigarette according to claim 13, wherein the housing is configured to define, in a use configuration of the electronic cigarette, air passage and distribution grooves which are adapted to be aligned with the plurality of portions of aromatic substance and in communication with air inlets leading to an end of the electronic cigarette.

17. The electronic cigarette according to claim 13, wherein the housing has a main direction of extension coinciding with a direction of insertion of the electric cartridge into the electronic cigarette and a transversal cross section configured to define the distribution grooves which, in the use configuration of the electronic cigarette, are delimited by walls of the housing and by the electric cartridge.

18. The electronic cigarette according to claim 16, wherein the housing comprises fixing cavities adapted to keep the electric cartridge in place in the use configuration of the electronic cigarette.

19. The electronic cigarette according to claim 13 and comprising an electric cartridge, wherein the electric power supply comprises a battery and wherein the housing comprises a plurality of radial portions, each adapted to receive a pair of panels of the electric cartridge in a use configuration of the electronic cigarette, the battery being positioned between two radial portions of the housing and extending along a main direction of extension of the electronic cigarette coinciding with a direction of insertion of the electric cartridge.

20. An electric cartridge for an electronic cigarette, comprising:
a piece of flexible substrate material comprising a flexible film which mounts an electrically conductive network in formed as an array and defining a plurality of resistive zones and a plurality of power supply pins for supplying one or more electric currents and connected to the plurality of resistive zones;
the plurality of resistive zones defining a heating device and being grouped into distinct modules, each of the distinct modules corresponding to an uninterrupted portion of the electrically conductive network and comprising a resistive zone of the plurality of resistive zones and respective ones of the plurality of power supply pins;
a plurality of portions of aromatic substance positioned on a face of the piece of flexible material, each of the plurality of portions being associated with the resistive zone and positioned in proximity to a heating surface of the resistive zone;
wherein the plurality of portions of aromatic substance are obtained by a deposition head which sprays a composite containing the aromatic substance;
wherein a portion of the plurality of portions of aromatic substance comprises two or more superposed or juxtaposed layers, each layer comprising a predetermined aromatic substance and made by one depositing pass.

* * * * *